(12) United States Patent
Okamura et al.

(10) Patent No.: US 7,943,311 B2
(45) Date of Patent: May 17, 2011

(54) KITS AND METHOD FOR DETERMINING THE RISK OF ADVERSE EFFECTS OF IRINOTECAN COMPRISING HYBRIDIZING PAIRS OF NUCLEIC ACID PROBES

(75) Inventors: Hiroshi Okamura, Kudamatsu (JP); Naoko Nakazawa, Kudamatsu (JP); Masaaki Oka, Ube (JP); Shouichi Hazama, Ube (JP)

(73) Assignees: Toyo Kohan Co., Ltd., Tokyo (JP); Yamaguchi University, Yamaguchi-shi (JP)

( * ) Notice: Subject to any disclaimer, the term of this patent is extended or adjusted under 35 U.S.C. 154(b) by 414 days.

(21) Appl. No.: 11/857,064

(22) Filed: Sep. 18, 2007

(65) Prior Publication Data

US 2008/0153093 A1    Jun. 26, 2008

(30) Foreign Application Priority Data

Sep. 19, 2006  (JP) ................................ 2006-253066

(51) Int. Cl.
*C12Q 1/68* (2006.01)
*C12P 19/34* (2006.01)

(52) U.S. Cl. .......................................... 435/6; 435/91.2

(58) Field of Classification Search .............. 435/6, 91.2
See application file for complete search history.

(56) References Cited

U.S. PATENT DOCUMENTS

| 6,274,310 | B1 * | 8/2001 | Habener et al. ................... 435/6 |
| 7,582,427 | B2 * | 9/2009 | Sato et al. ......................... 435/6 |
| 2004/0058363 | A1 * | 3/2004 | Hasegawa et al. ................ 435/6 |
| 2004/0203034 | A1 * | 10/2004 | Ratain et al. ..................... 435/6 |
| 2006/0160074 | A1 * | 7/2006 | Dorn et al. ........................ 435/6 |

OTHER PUBLICATIONS

Meinkoth et al., Analytical Biochemistry 138, 267-284 (1984).*
Han et al, Journal of Clinical Oncology, 2006, 24(15), pp. 2237-2244.
Smith at al, Toxicology in Vitro, 2006, 20, pp. 163-175.
Yuichi Ando, et al., "Polymorphisms of UDP-Glucuronosyltransferase Gene and Irinotecan Toxicity: A Pharamacogenetic Analysis[1]", Cancer Research, vol. 60, Dec. 15, 2000, pp. 6921-6926.

* cited by examiner

*Primary Examiner* — Kenneth R. Horlick
(74) *Attorney, Agent, or Firm* — Oblon, Spivak, McClelland, Maier & Neustadt, L.L.P.

(57) ABSTRACT

A method for determining the risk of adverse effects of irinotecan (CPT-11), a synthetic anticancer drug, by detecting polymorphisms in the TATA box within the promoter region of the UDP-glucuronosyl transferase gene. A kit for detecting the adverse effects of irinotecan containing at least one pair of nucleic acid probes.

16 Claims, 6 Drawing Sheets

| | ① | ② | ③ |
|---|---|---|---|
| 50 mer PROBES 1 & 2 | | | |
| 30 mer PROBES 3 & 4 | | | |
| 20 mer PROBES 5 & 6 | | | |

GENOTYPES OF SAMPLES
① TA6/TA6
② TA6/TA7
③ TA7/TA7

← PROBES 1, 3, 5 (TA × 7)
← PROBES 2, 4, 6 (TA × 6)

GENOTYPES OF SAMPLES
① TA6/TA6
② TA6/TA7
③ TA7/TA7

Fig. 5

| | ① | ② | ③ |
|---|---|---|---|
| TA7 PROBE 3 | | | |
| TA6 PROBE 11 | | | |
| TA8 PROBE 12 | | | |
| TA5 PROBE 13 | | | |

GENOTYPES OF SAMPLES
① TA6/TA6
② TA6/TA7
③ TA7/TA7

KITS AND METHOD FOR DETERMINING THE RISK OF ADVERSE EFFECTS OF IRINOTECAN COMPRISING HYBRIDIZING PAIRS OF NUCLEIC ACID PROBES

BACKGROUND OF THE INVENTION

1. Field of the Invention

The present invention relates to a method for determining the risk of adverse effects of irinotecan and a kit for it.

2. Background Art

Irinotecan (CPT-11) is a synthetic anticancer agent derived from the antitumor alkaloid camptothecin originally isolated from *Camptotheca acuminata* and is shown to be effective in treating cancers such as lung cancer and metastatic colon carcinoma. While irinotecan demonstrates strong anticarcinoma activity by inhibiting topoisomerase, which promotes DNA replication, it is reported that significant toxicity of irinotecan can induce adverse effects such as leucopenia and diarrhea.

The enzyme UDP-glucuronosyl transferase (UGT) catalyzes glucuronidation reactions of drugs as well as exogenous and endogenous substances such as bilirubin, steroid hormones and bile acid. One of the genes encoding the enzyme is called UGT1A1, which is known to have polymorphisms.

It is reported that polymorphisms in the UGT1A1 gene are related to the occurrence of adverse effects of the anticancer agent irinotecan (CPT-11). More specifically, patients with UGT1A1 polymorphisms resulting in reduced UGT activity are found to have a greater risk of developing serious adverse effects such as leucopenia and severe diarrhea. One of the polymorphisms in the UGT1A1 gene designated as UGT1A1*28A has 7 TA repeats in the TATA box within the promoter region in stead of 6 repeats in the predominant wild type designated as UGT1A1*1. The insertion of these extra two nucleotides (TA) in the variant allele accounts for lowered gene expression of UGT1A1 and results in reduced UGT activity.

Therefore, the detection of UGT1A1 polymorphisms has been expected to serve as an effective means to predict and prevent adverse effects of irinotecan. Conventional methods for polymorphism detection include direct sequencing and fragment analysis. Furthermore, Invader UGT1A1 Molecular Assay for Irinotecan Toxicity (Third Wave Technologies, Inc., USA) is in practical use as a diagnostic product for the detection of UGT1A1 polymorphisms. Unfortunately, a problem with the methods above is that they lack sufficient detection accuracy and they are not cost-effective in detecting the polymorphisms.

SUMMARY OF THE INVENTION

It is an object of the present invention to provide simple and efficient means for determining the risk of adverse effects of irinotecan by detecting polymorphisms in the UDP-glucuronosyl transferase gene.

The present inventors have done earnest research and found that polymorphisms in the UGT1A1 gene can be efficiently determined by a hybridization method, using nucleic acid probes wherein each of the nucleic acid probes comprises either a nucleotide sequence of 25 to 35 contiguous nucleotides including the TATA box within the promoter region of the UDP-glucuronosyl transferase gene (UGT1A1 gene), the above described nucleotide sequence of 25 to 35 contiguous nucleotides with an altered number of TA repeats in the TATA box, or the complementary sequence to one of the above. Based on this scientific knowledge, the inventors have achieved the present invention.

More specifically, the present invention comprises the following specific inventions.

1. A method for determining the risk of adverse effects of irinotecan by detecting polymorphisms in the TATA box within the promoter region of the UDP-glucuronosyl transferase gene, wherein at least one of the nucleic acid probe pairs selected from the group consisting Nucleic Acid Probes a and b, c and d, e and f, a and f, and e and b described below is hybridized to amplified nucleic acids obtained by amplification of the template genomic DNA isolated from a biological sample obtained from a subject and wherein the ratio between the amount of nucleic acids hybridized to Nucleic Acid Probe a and the amount of nucleic acids hybridized to Nucleic Acid Probe b, the ratio between the amount of nucleic acids hybridized to Nucleic Acid Probe c and the amount of nucleic acids hybridized to Nucleic Acid Probe d, the ratio between the amount of nucleic acids hybridized to Nucleic Acid Probe e and the amount of nucleic acids hybridized to Nucleic Acid Probe f, the ratio between the amount of nucleic acids hybridized to Nucleic Acid Probe a and the amount of nucleic acids hybridized to Nucleic Acid Probe f, and/or the ratio between the amount of nucleic acids hybridized to Nucleic Acid Probe e and the amount of nucleic acids hybridized to Nucleic Acid Probe b are measured:

a. A nucleic acid probe which consists of a nucleotide sequence of 25 to 35 contiguous nucleotides including 14 nucleotides from No. 439 to No. 452 in the nucleotide sequence represented by SEQ ID NO:1;

b. A nucleic acid probe which consists of a nucleotide sequence of 25 to 35 contiguous nucleotides including 12 nucleotides from No. 439 to No. 450 in the nucleotide sequence represented by SEQ ID NO:2;

c. A nucleic acid probe which consists of a complementary sequence to the nucleotide sequence of 25 to 35 contiguous nucleotides including the 14 nucleotides from No. 439 to No. 452 in the nucleotide sequence represented by SEQ ID NO:1;

d. A nucleic acid probe which consists of a complementary sequence to the nucleotide sequence of 25 to 35 contiguous nucleotides including the 12 nucleotides from No. 439 to No. 450 in the nucleotide sequence represented by SEQ ID NO:2;

e. A nucleic acid probe which consists of a nucleotide sequence of 25 to 35 contiguous nucleotides including 16 nucleotides, 8 TA repeats, (TATATATATATATATA) replacing the 14 nucleotides from No. 439 to No. 452 in the nucleotide sequence represented by SEQ ID NO:1;

f. A nucleic acid probe which consists of a nucleotide sequence of 25 to 35 contiguous nucleotides including 10 nucleotides, 5 TA repeats, (TATATATATA) replacing the 12 nucleotides from No. 439 to No. 450 in the nucleotide sequence represented by SEQ ID NO:2.

2. The present invention provides a method for determining the risk of adverse effects of irinotecan in subjects, wherein the method described above comprises the steps for:

1) amplifying the region including the TATA box within the promoter region of the UDP-glucuronosyl transferase gene, using the template genomic DNA isolated from a sample obtained from a subject;

2) hybridizing the amplified nucleic acids obtained in Step 1 to at least one of the nucleic acid probe pairs selected from the group consisting Nucleic Acid Probes a and b, c and d, e and f, a and f, and e and b described below:

a. A nucleic acid probe which consists of a nucleotide sequence of 25 to 35 contiguous nucleotides including 14 nucleotides from No. 439 to No. 452 in the nucleotide sequence represented by SEQ ID NO:1;
b. A nucleic acid probe which consists of a nucleotide sequence of 25 to 35 contiguous nucleotides including 12 nucleotides from No. 439 to No. 450 in the nucleotide sequence represented by SEQ ID NO:2;
c. A nucleic acid probe which consists of a complementary sequence to the nucleotide sequence of 25 to 35 contiguous nucleotides including the 14 nucleotides from No. 439 to No. 452 in the nucleotide sequence represented by SEQ ID NO:1;
d. A nucleic acid probe which consists of a complementary sequence to the nucleotide sequence of 25 to 35 contiguous nucleotides including the 12 nucleotides from No. 439 to No. 450 in the nucleotide sequence represented by SEQ ID NO:2;
e. A nucleic acid probe which consists of a nucleotide sequence of 25 to 35 contiguous nucleotides including 16 nucleotides, 8 TA repeats, (TATATATATATATATA) replacing the 14 nucleotides from No. 439 to No. 452 in the nucleotide sequence represented by SEQ ID NO:1;
f. A nucleic acid probe which consists of a nucleotide sequence of 25 to 35 contiguous nucleotides including 10 nucleotides, 5 TA repeats, (TATATATATA) replacing the 12 nucleotides from No. 439 to No. 450 in the nucleotide sequence represented by SEQ ID NO:2.

3) measuring the ratio between the amount of nucleic acids hybridized to Nucleic Acid Probe a and the amount of nucleic acids hybridized to Nucleic Acid Probe b, the ratio between the amount of nucleic acids hybridized to Nucleic Acid Probe c and the amount of nucleic acids hybridized to Nucleic Acid Probe d, the ratio between the amount of nucleic acids hybridized to Nucleic Acid Probe e and the amount of nucleic acids hybridized to Nucleic Acid Probe f, the ratio between the amount of nucleic acids hybridized to Nucleic Acid Probe a and the amount of nucleic acids hybridized to Nucleic Acid Probe f, and/or the ratio between the amount of nucleic acids hybridized to Nucleic Acid Probe e and the amount of nucleic acids hybridized to Nucleic Acid Probe b.

3. The method described in reference numeral 1 or 2, wherein Nucleic Acid Probe a includes the nucleotide sequence represented by SEQ ID NO:3 and Nucleic Acid Probe b includes the nucleotide sequence represented by either SEQ ID NO:4 or NO:17, or alternatively
Nucleic Acid Probe a includes the nucleotide sequence represented by SEQ ID NO:5 and Nucleic Acid Probe b includes the nucleotide sequence represented by SEQ ID NO:6.

4. The method described in reference numeral 1 or 2, wherein Nucleic Acid Probe c includes the nucleotide sequence represented by SEQ ID NO:7 and Nucleic Acid Probe d includes the nucleotide sequence represented by SEQ ID NO: 8, or alternatively
Nucleic Acid Probe c includes the nucleotide sequence represented by SEQ ID NO:9 and Nucleic Acid Probe d includes the nucleotide sequence represented by SEQ ID NO:10.

5. The method described in reference numeral 1 or 2, wherein Nucleic Acid Probe e includes the nucleotide sequence represented by SEQ ID NO:18 and Nucleic Acid Probe f includes the nucleotide sequence represented by SEQ ID NO:19.

6. The method described in reference numeral 1 or 2, wherein Nucleic Acid Probe a consists of the nucleotide sequence represented by SEQ ID NO:3 with one or two-nucleotide deletion at its 3' and/or 5' end and Nucleic Acid Probe b consists of the nucleotide sequence represented by either SEQ ID NO:4 or NO:17 with one or two-nucleotide deletion at its 3' and/or 5' end, or alternatively
Nucleic Acid Probe a consists of the nucleotide sequence represented by SEQ ID NO:5 with one or two-nucleotide deletion at its 3' and/or 5' end and Nucleic Acid Probe b consists of the nucleotide sequence represented by SEQ ID NO:6 with one or two-nucleotide deletion at its 3' and/or 5' end.

7. The method described in reference numeral 1 or 2, wherein Nucleic Acid Probe c consists of the nucleotide sequence represented by SEQ ID NO:7 with one or two-nucleotide deletion at its 3' and/or 5' end and Nucleic Acid Probe d consists of the nucleotide sequence represented by SEQ ID NO:8 with one or two-nucleotide deletion at its 3' and/or 5' end, or alternatively
Nucleic Acid Probe c consists of the nucleotide sequence represented by SEQ ID NO:9 with one or two-nucleotide deletion at its 3' and/or 5' end and Nucleic Acid Probe d consists of the nucleotide sequence represented by SEQ ID NO:10 with one or two-nucleotide deletion at its 3' and/or 5' end.

8. The method described in reference numeral 1 or 2, wherein Nucleic Acid Probe e consists of the nucleotide sequence represented by SEQ ID NO:18 with one or two-nucleotide deletion at its 3' and/or 5' end and Nucleic Acid Probe f consists of the nucleotide sequence represented by SEQ ID NO:19 with one or two-nucleotide deletion at its 3' and/or 5' end.

9. A kit used to detect adverse effects of irinotecan, which includes at least one of the nucleic acid probe pairs selected from the group consisting Nucleic Acid Probes a and b, c and d, e and f, a and f, and e and b described below:
a. A nucleic acid probe which consists of a nucleotide sequence of 25 to 35 contiguous nucleotides including 14 nucleotides from No. 439 to No. 452 in the nucleotide sequence represented by SEQ ID NO:1;
b. A nucleic acid probe which consists of a nucleotide sequence of 25 to 35 contiguous nucleotides including 12 nucleotides from No. 439 to No. 450 in the nucleotide sequence represented by SEQ ID NO:2;
c. A nucleic acid probe which consists of a complementary sequence to the nucleotide sequence of 25 to 35 contiguous nucleotides including the 14 nucleotides from No. 439 to No. 452 in the nucleotide sequence represented by SEQ ID NO:1;
d. A nucleic acid probe which consists of a complementary sequence to the nucleotide sequence of 25 to 35 contiguous nucleotides including the 12 nucleotides from No. 439 to No. 450 in the nucleotide sequence represented by SEQ ID NO:2;
e. A nucleic acid probe which consists of a nucleotide sequence of 25 to 35 contiguous nucleotides including 16 nucleotides, 8 TA repeats, (TATATATATATATATA) replacing the 14 nucleotides from No. 439 to No. 452 in the nucleotide sequence represented by SEQ ID NO:1;
f. A nucleic acid probe which consists of a nucleotide sequence of 25 to 35 contiguous nucleotides including 10 nucleotides, 5 TA repeats, (TATATATATA) replacing the 12 nucleotides from No. 439 to No. 450 in the nucleotide sequence represented by SEQ ID NO:2.

10. The kit described in reference numerical 9, comprising a microarray with the nucleic acid probes immobilized on a carrier.

11. The kit described in reference numerical 9 or 10, wherein
Nucleic Acid Probe a includes the nucleotide sequence
represented by SEQ ID NO:3 and Nucleic Acid Probe b
includes the nucleotide sequence represented by either
SEQ ID NO:4 or NO:17, or alternatively
Nucleic Acid Probe a includes the nucleotide sequence
represented by SEQ ID NO:5 and Nucleic Acid Probe b
includes the nucleotide sequence represented by SEQ ID
NO:6.
12. The kit described in reference numerical 9 or 10, wherein
Nucleic Acid Probe c includes the nucleotide sequence
represented by SEQ ID NO:7 and Nucleic Acid Probe d
includes the nucleotide sequence represented by SEQ ID
NO:8, or alternatively
Nucleic Acid Probe c includes the nucleotide sequence
represented by SEQ ID NO:9 and Nucleic Acid Probe d
includes the nucleotide sequence represented by SEQ ID
NO:10.
13. The kit described in reference numerical 9 or 10, wherein
Nucleic Acid Probe e includes the nucleotide sequence
represented by SEQ ID NO:18 and Nucleic Acid Probe f
includes the nucleotide sequence represented by SEQ ID
NO:19.
14. The kit described in reference numerical 9 or 10, wherein
Nucleic Acid Probe a consists of the nucleotide sequence
represented by SEQ ID NO:3 with one or two-nucleotide
deletion at its 3' and/or 5' end and Nucleic Acid Probe b
consists of the nucleotide sequence represented by either
SEQ ID NO:4 or NO:17 with one or two-nucleotide deletion at its 3' and/or 5' end, or alternatively
Nucleic Acid Probe a consists of the nucleotide sequence
represented by SEQ ID NO:5 with one or two-nucleotide
deletion at its 3' and/or 5' end and Nucleic Acid Probe b
consists of the nucleotide sequence represented by SEQ ID
NO:6 with one or two-nucleotide deletion at its 3' and/or 5'
end.
15. The kit described in reference numerical 9 or 10, wherein
Nucleic Acid Probe c consists of the nucleotide sequence
represented by SEQ ID NO:7 with one or two-nucleotide
deletion at its 3' and/or 5' end and Nucleic Acid Probe d
consists of the nucleotide sequence represented by SEQ ID
NO:8 with one or two-nucleotide deletion at its 3' and/or 5'
end, or alternatively
Nucleic Acid Probe c consists of the nucleotide sequence
represented by SEQ ID NO:9 with one or two-nucleotide
deletion at its 3' and/or 5' end and Nucleic Acid Probe d
consists of the nucleotide sequence represented by SEQ ID
NO:10 with one or two-nucleotide deletion at its 3' and/or 5'
end.
16. The kit described in reference numerical 9 or 10, wherein
Nucleic Acid Probe e consists of the nucleotide sequence
represented by SEQ ID NO:18 with one or two-nucleotide
deletion at its 3' and/or 5' end and Nucleic Acid Probe f
consists of the nucleotide sequence represented by SEQ ID
NO:19 with one or two-nucleotide deletion at its 3' and/or
5' end.

The present invention enables the detection of polymorphisms in the UDP-glucuronosyl transferase gene with a high degree of accuracy and thus provides simple and efficient means to determine the risk of adverse effects of irinotecan.

This specification incorporates the content of the specification of Japanese Patent Application No. 2006-253066, for which priority is claimed to the present application.

BRIEF DESCRIPTION OF THE DRAWINGS

FIG. 5 shows fluorescent images of the amplified nucleic acids hybridized to the microarray manufactured according to Example 3, taken with a fluorescence scanner.

DETAILED DESCRIPTION OF THE PREFERRED EMBODIMENTS

Figure 1:
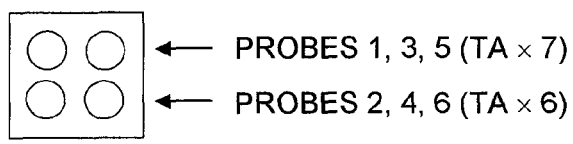
FIG. 1 shows the position of each nucleic acid probe spot on a microarray manufactured according to Example 1 as well as fluorescence images of the amplified nucleic acids hybridized to the microarray, taken with a fluorescence scanner.

In one embodiment, the present invention relates to a method for determining the risk of adverse effects of irinotecan by detecting polymorphisms in the TATA box within the promoter region of the UDP-glucuronosyl transferase gene.

Irinotecan (CPT-11), 1,4'-bipiperidine-1'-carboxylic acid (S)-4,11-diethyl-3,4,12,14-tetrahydro-4-hydroxy-3,14-dioxo-1H-pyrano[3',4':6,7]indolizino[1,2-b]quinolin-9-yl ester (CAS NO: 97682-44-5), is a synthetic compound derived from the antitumor alkaloid camptothecin originally isolated from *Camptotheca acuminate*. In the present invention, irinotecan may also be in the form of a salt thereof, a solvate thereof, particularly a hydrate thereof such as CAS NO: 136572-09-3 as a typical example. Pharmaceutically acceptable acid addition salts of irinotecan are preferably used as anticancer agents. Examples of such acid addition salts include acid addition salts with inorganic acids such as hydrochloric acid, sulfuric acid, phosphoric acid, and hydrobromic acid; acid addition salts with organic acids such as oxalic acid, maleic acid, fumaric acid, malic acid, tartaric acid, citric acid, benzoic acid, acetic acid, p-toluenesulfonic acid, and methanesulfonic acid. In particular, hydrochloride thereof (irinotecan hydrochloride; CAS NO: 136572-09-3) is preferably used.

Irinotecan is metabolized to form an active metabolite, SN-38, by carboxylesterase, following in vivo administration SN-38 is further conjugated and detoxified by UDP-glucuronosyl transferase (UGT) in the liver and finally processed for intestinal excretion. The relative balance of UGT activity for detoxification of SN-38 determines the level of SN-38 in vivo. As a result, it is considered that difference in SN-38 exposure level translates into individual variability in the magnitude of adverse effects of irinotecan. The primary detoxification pathway for SN-38 is glucuronidation and it is shown that SN-38 glucuronidation is mainly catalyzed by UGT1A1, which is a UGT molecular species. Patients with UGT1A1 polymorphisms are more likely to suffer from severe adverse effects following irinotecan administration due to lowered UGT activity, resulting in delayed detoxification of SN-38. A polymorphism in the UGT1A1 gene designated as UGT1A1*28A has 7 TA repeats in the TATA box within the promoter region in stead of 6 repeats in the predominant wild type designated as UGT1A1*1. The insertion of these extra two nucleotides (TA) in the variant allele accounts for lowered gene expression of UGT1A1 and results in reduced UGT activity.

The adverse effects of irinotecan in the present invention may be adverse effects occurring in patients to whom irinotecan is administered, wherein the adverse effects have a higher likelihood of occurrence in the patients with variations in the UDP-glucuronosyl transferase gene without being limited. Preferably, the adverse effects may be adverse effects which have a higher likelihood of occurrence in the patients with variations in the UGT1A1 gene. More particularly, the adverse effects may be adverse effects which have a higher likelihood of occurrence in the patients with UGT1A1*28. In other words, the adverse effects of irinotecan in the present invention comprise adverse effects whose likelihoods of occurrence are elevated by lowered gene expression of the UDP-glucuronosyl transferase gene and/or reduced activity of UDP-glucuronosyl transferase. More specifically, examples of adverse effects of irinotecan include myelotoxicity such as leucopenia, diarrhea, vomiting, general malaise, anorexia and alopecia.

UDP-glucuronosyl transferase (UGT) is a transmembrane enzyme, which is mainly localized in the endoplasmic reticulum of the liver. UGT is a protein which catalyzes glucuronidation reactions that transfer glucuronic acid on foreign lipophilic compounds inside or outside the organism such as drugs, environmental pollutants and food additives. The nucleotide sequence of UGT1A1, which is a molecular species of UDP-glucuronosyl transferase (UGT), and its corresponding amino acid sequence are registered in public databases (GenBank, EMBL, DDBJ) under Accession No. NM_000463. The wild-type nucleotide sequence of the promoter region of the UDP-glucuronosyl transferase gene, which has 6 TA repeats in the TATA box, is registered in public databases (GenBank, EMBL, DDBJ) under Accession No: AY533179 (SEQ ID NO:2). The nucleotide sequence of the variant allele of the promoter region of the UDP-glucuronosyl transferase gene, which has 7 TA repeats in the TATA box, is registered in public databases (GenBank, EMBL, DDBJ) under Accession No: AY533180 (SEQ ID NO:1). For example, each sequence can be retrieved from the Internet: URL: http://www.ncbi.nlm.nih.gov/.

The method for determining the risk of adverse effects of irinotecan in the present invention is characterized in that any pair of the nucleic acid probes selected from Nucleic Acid Probes a and b, c and d, e and f, a and f, and/or e and b described below is hybridized to amplified nucleic acids obtained by amplification of the template genomic DNA isolated from a biological sample obtained from a subject, generally a human subject and the ratio between the amount of nucleic acids hybridized to Nucleic Acid Probe a and the amount of nucleic acids hybridized to Nucleic Acid Probe b, the ratio between the amount of nucleic acids hybridized to Nucleic Acid Probe c and the amount of nucleic acids hybridized to Nucleic Acid Probe d, the ratio between the amount of nucleic acids hybridized to Nucleic Acid Probe e and the amount of nucleic acids hybridized to Nucleic Acid Probe f, the ratio between the amount of nucleic acids hybridized to Nucleic Acid Probe a and the amount of nucleic acids hybridized to Nucleic Acid Probe f, and/or the ratio between the amount of nucleic acids hybridized to Nucleic Acid Probe e and the amount of nucleic acids hybridized to Nucleic Acid Probe b are measured:

a. A nucleic acid probe which comprises a nucleotide sequence of 25 to 35 contiguous nucleotides, more preferably 27 to 33 contiguous nucleotides, even more preferably 29 to 31 contiguous nucleotides including 14 nucleotides from No. 439 to No. 452 in the nucleotide sequence represented by SEQ ID NO:1;

b. A nucleic acid probe which comprises a nucleotide sequence of 25 to 35 contiguous nucleotides, more preferably 27 to 33 contiguous nucleotides, even more preferably 29 to 31 contiguous nucleotides including 12 nucleotides from No. 439 to No. 450 in the nucleotide sequence represented by SEQ ID NO:2;

c. A nucleic acid probe which comprises a complementary sequence to a nucleotide sequence of 25 to 35 contiguous nucleotides, more preferably 27 to 33 contiguous nucleotides, even more preferably 29 to 31 contiguous nucleotides including 14 nucleotides from No. 439 to No. 452 in the nucleotide sequence represented by SEQ ID NO:1;

d. A nucleic acid probe which comprises a complementary sequence to a nucleotide sequence of 25 to 35 contiguous nucleotides, more preferably 27 to 33 contiguous nucleotides, even more preferably 29 to 31 contiguous nucleotides including 12 nucleotides from No. 439 to No. 450 in the nucleotide sequence represented by SEQ ID NO:2;

e. A nucleic acid probe which comprises a nucleotide sequence of 25 to 35 nucleotides comprising 16 nucleotides, 8 TA repeats, (TATATATATATATATA) replacing the 14 nucleotides from No. 439 to No. 452 in the nucleotide sequence represented by SEQ ID NO:1;

f. A nucleic acid probe which comprises a nucleotide sequence of 25 to 35 nucleotides including 10 nucleotides, 5 TA repeats, (TATATATATA) replacing the 12 nucleotides from No. 439 to No. 450 in the nucleotide sequence represented by SEQ ID NO:2. Nucleic Acid Probes may be sometimes abbreviated as probes hereinafter.

At least one or all of the following ratios may be measured: the ratio between the amount of nucleic acids hybridized to Nucleic Acid Probe a and the amount of nucleic acids hybridized to Nucleic Acid Probe b, the ratio between the amount of nucleic acids hybridized to Nucleic Acid Probe c and the amount of nucleic acids hybridized to Nucleic Acid Probe d, the ratio between the amount of nucleic acids hybridized to Nucleic Acid Probe e and the amount of nucleic acids hybridized to Nucleic Acid Probe f, the ratio between the amount of nucleic acids hybridized to Nucleic Acid Probe a and the amount of nucleic acids hybridized to Nucleic Acid Probe f, and the ratio between the amount of nucleic acids hybridized to Nucleic Acid Probe e and the amount of nucleic acids hybridized to Nucleic Acid Probe b. Detection accuracy can be enhanced by taking as many of the ratios described above as possible. The nucleic acids in the present invention comprise both DNAs and RNAs, wherein the DNAs comprise single-stranded DNAs as well as double-stranded DNAs. The nucleic acid probes in the present invention are preferably DNAs. The amplified nucleic acids in the present invention are preferably DNAs.

The amplified nucleic acids obtained by amplification of the template genomic DNA isolated from a biological sample obtained from a subject generally may be amplified nucleic acids obtained by amplifying the region including the TATA box within the promoter region of the UDP-glucuronosyl transferase gene with the use of the template genomic DNA isolated from a biological sample obtained from a subject. The region including the TATA box within the promoter region of the UDP-glucuronosyl transferase gene comprises a region which includes at least the TATA box within the promoter region of the UDP-glucuronosyl transferase gene.

Therefore, more specifically, the method for determining the risk of adverse effects of irinotecan in the present invention comprises the steps of:

1) amplifying the region including the TATA box within the promoter region of the UDP-glucuronosyl transferase gene, using template genomic DNAs isolated from samples obtained from the subjects;
2) hybridizing the amplified nucleic acid obtained according to Step 1 above to the nucleic acid probes a and b, c and d, e and f, a and f, and/or e and b described above;
3) measuring the ratio between the amount of nucleic acids hybridized to Nucleic Acid Probe a and the amount of nucleic acids hybridized to Nucleic Acid Probe b, the ratio between the amount of nucleic acids hybridized to Nucleic Acid Probe c and the amount of nucleic acids hybridized to Nucleic Acid Probe d, the ratio between the amount of nucleic acids hybridized to Nucleic Acid Probe e and the amount of nucleic acids hybridized to Nucleic Acid Probe f, the ratio between the amount of nucleic acids hybridized to Nucleic Acid Probe a and the amount of nucleic acids hybridized to Nucleic Acid Probe f, and/or the ratio between the amount of nucleic acids hybridized to Nucleic Acid Probe e and the amount of nucleic acids hybridized to Nucleic Acid Probe b.

A pair of nucleic acid probes, which is used to measure the ratio between the amounts of nucleic acids hybridized to the probes, is preferably of the same length. For example, it is preferable to use probes of the same length for any of the nucleic acid probe pairs selected from Nucleic Acid Probes a and b, c and d, e and f, a and f, and e and b. For any pair of nucleic acid probes, which is used to measure the ratio between the amounts of nucleic acids hybridized to the probes, it is also preferable to use probes designed to have the same number of nucleotides between the end of the TATA box and the terminal of each probe, wherein the terminal is generally a terminal which is not immobilized on the carrier in a microarray (3' end or 5' end). For example, it is preferable to design Nucleic Acid Probes a and b to have the same number of nucleotides between the end of the TATA box and the terminal. The number of nucleotides between the end of TATA box and the terminal is generally 1 to 12, preferably 2 to 10, and more preferably 4 to 8.

Specific examples of Nucleic Acid Probe a include nucleic acid probes which contain the nucleotide sequence represented by either SEQ ID NO:3 or NO:5. Specific examples of Nucleic Acid Probe b include nucleic acid probes which contain the nucleotide sequence represented by either SEQ ID NO:4, NO: 17 or NO:6. Specific examples of Nucleic Acid Probe c include nucleic acid probes which contain the nucleotide sequence represented by either SEQ ID NO:7 or NO:9. Specific examples of Nucleic Acid Probe d include nucleic acid probes which contain the nucleotide sequence represented by either SEQ ID NO:8 or NO:10. Specific examples of Nucleic Acid Probe e include nucleic acid probes which contain the nucleotide sequence represented by SEQ ID NO:18. Specific examples of Nucleic Acid Probe f include nucleic acid probes which contain the nucleotide sequence represented by SEQ ID NO:19. The nucleic acid probes described above have preferably less than 33 nucleotide length, and more preferably less than 31 nucleotide length.

It is preferable to use a pair of Nucleic Acid Probe a including the nucleotide sequence represented by SEQ ID NO:3 and Nucleic Acid Probe b including the nucleotide sequence represented by either SEQ ID NO:4 or NO:17 and measure the ratio between the amounts of amplified nucleic acids hybridized to the probes. It is also preferable to use a pair of Probe a including the nucleotide sequence represented by SEQ ID NO:5 and Nucleic Acid Probe b including the nucleotide sequence represented by SEQ ID NO:6 and measure the ratio between the amounts of amplified nucleic acids hybridized to the probes.

It is preferable to use a pair of Nucleic Acid Probe c including the nucleotide sequence represented by SEQ ID NO:7 and Nucleic Acid Probe d including the nucleotide sequence represented by SEQ ID NO:8 and measure the ratio between the amounts of amplified nucleic acids hybridized to the probes. It is also preferable to use a pair of Nucleic Acid Probe c including the nucleotide sequence represented by SEQ ID NO:9 and Nucleic Acid Probe d including the nucleotide sequence represented by SEQ ID NO:10 and measure the ratio between the amounts of amplified nucleic acids hybridized to the probes.

It is preferable to use a pair of Nucleic Acid Probe e including the nucleotide sequence represented by SEQ ID NO:18 and Nucleic Acid Probe f including the nucleotide sequence represented by SEQ ID NO:19 and measure the ratio between the amounts of amplified nucleic acids hybridized to the probes.

Other specific examples of Nucleic Acid Probe a include nucleic acid probes which comprise the nucleotide sequence represented by either SEQ ID NO:3 or NO:5 with one or two-nucleotide deletion at their 3' and/or 5' end. Other specific examples of Nucleic Acid Probe b include nucleic acid probes which comprise the nucleotide sequence represented by either SEQ ID NO:4, NO: 17 or NO:6 with one or two-nucleotide deletion at their 3' and/or 5' end. Other specific examples of Nucleic Acid Probe c include nucleic acid probes which comprise the nucleotide sequence represented by either SEQ ID NO:7 or NO:9 with one or two-nucleotide deletion at their 3' and/or 5' end. Other specific examples of Nucleic Acid Probe d include nucleic acid probes which comprise the nucleotide sequence represented by either SEQ ID NO:8 or NO:10 with one or two-nucleotide deletion at their 3' and/or 5' end. Other specific examples of Nucleic Acid Probe e include nucleic acid probes which comprise the nucleotide sequence represented by SEQ ID NO:18 with one or two-nucleotide deletion at their 3' and/or 5' end. Other specific examples of Nucleic Acid Probe f include nucleic acid probes which comprise the nucleotide sequence represented by SEQ ID NO:19 with one or two-nucleotide deletion at their 3' and/or 5' end. For any pair of nucleic acid probes, which is used to measure the ratio between the amounts of nucleic acids hybridized to the probes, it is preferable to use nucleic acid probes which have the same size deletion and have a deletion on the same side of the sequence (3' end or 5' end).

It is preferable to use a pair of Nucleic Acid Probe a comprising the nucleotide sequence represented by SEQ ID NO:3 with one or two-nucleotide deletion at its 3' and/or 5' end and Nucleic Acid Probe b comprising the nucleotide sequence represented by either SEQ ID NO:4 or NO: 17 with one or two-nucleotide deletion at its 3' and/or 5' end and measure the ratio between the amounts of amplified nucleic acids hybridized to the probes. It is preferable to use a pair of Nucleic Acid Probe a comprising the nucleotide sequence represented by SEQ ID NO:5 with one or two-nucleotide deletion at its 3' and/or 5' end and Nucleic Acid Probe b comprising the nucleotide sequence represented by SEQ ID NO:6 with one or two-nucleotide deletion at its 3' and/or 5' end and measure the ratio between the amounts of amplified nucleic acids hybridized to the probes.

It is preferable to use a pair of Nucleic Acid Probe c comprising the nucleotide sequence represented by SEQ ID NO:7 with one or two-nucleotide deletion at its 3' and/or 5' end and Nucleic Acid Probe d comprising the nucleotide sequence represented by SEQ ID NO:8 with one or two-nucleotide deletion at its 3' and/or 5' end and measure the ratio between the amounts of amplified nucleic acids hybridized to the probes. It is preferable to use a pair of Nucleic Acid Probe c comprising the nucleotide sequence represented by SEQ ID NO:9 with one or two-nucleotide deletion at its 3' and/or 5' end and Nucleic Acid Probe d comprising the nucleotide sequence represented by SEQ ID NO:10 with one or two-nucleotide deletion at its 3' and/or 5' end and measure the ratio between the amounts of amplified nucleic acids hybridized to the probes.

It is preferable to use a pair of Nucleic Acid Probe e comprising the nucleotide sequence represented by SEQ ID NO:18 with one or two-nucleotide deletion at its 3' and/or 5' end and Nucleic Acid Probe f comprising the nucleotide sequence represented by SEQ ID NO:19 with one or two-nucleotide deletion at its 3' and/or 5' end and measure the ratio between the amounts of amplified nucleic acids hybridized to the probes.

The nucleic acid probes can be obtained by chemical synthesis, using a nucleic acid synthesis machine, wherein the nucleic acid synthesis machine can be any machine named DNA synthesizer, fully automated nucleic acid synthesis machine, and automatic nucleic acid synthesis apparatus.

The ratio between the amounts of nucleic acids hybridized to Nucleic Acid Probes a and b determines the UGT1A1 genotypes of the subjects. More specifically, the subjects are categorized to one of the following three genotypes: the wild type in which both alleles have 6 TA repeats in the TATA box (TA6/TA6); heterozygous variant type, carrying one variant allele with 7 TA repeats and one wild-type allele described above (TA6/TA7); homozygous variant type, carrying two variant allele described above (TA7/TA7). This as a result enables to predict the risk of adverse effects of irinotecan. More specifically, the larger the ratio of the amount of nucleic acids hybridized to Nucleic Acid Probe b to the amount of nucleic acids hybridized to Nucleic Acid Probe a, the smaller the risk of adverse effects of irinotecan. In more detail, samples from a group of patients whose genotypes had been determined are subjected to nucleic acid hybridization, using Nucleic Acid Probes a and b. A standard value was calculated by statistical procedure for each genotype above. By comparing the ratio for the subjects with unknown genotypes with the standard values described above, one can determine the genotypes of the subjects and predict the risk of adverse effects of irinotecan. The same is true in the case of Nucleic Acid Probes c and d. The larger the ratio of the amount of nucleic acids hybridized to Nucleic Acid Probe d to the amount of nucleic acids hybridized to Nucleic Acid Probe c, the smaller the risk of adverse effects of irinotecan.

The ratio between the amounts of nucleic acids hybridized to Nucleic Acid Probes e and f can also determine the UGT1A1 genotypes of the subjects and predict the risk of adverse effects of irinotecan. More specifically, the larger the ratio of the amount of nucleic acids hybridized to Nucleic Acid Probe f to the amount of nucleic acids hybridized to Nucleic Acid Probe e, the smaller the risk of adverse effects of irinotecan.

The ratio between the amounts of nucleic acids hybridized to Nucleic Acid Probes a and f as well as Nucleic Acid Probes e and b can also predict the risk of adverse effects of irinotecan in the same manner. The larger the ratio of the amount of nucleic acids hybridized to Nucleic Acid Probe f to the amount of nucleic acids hybridized to Nucleic Acid Probe a, the smaller the risk of adverse effects of irinotecan. The larger the ratio of the amount of nucleic acids hybridized to Nucleic Acid Probe b to the amount of nucleic acids hybridized to Nucleic Acid Probe e, the smaller the risk of adverse effects of irinotecan.

The samples obtained from the subjects include, without limitation to, genomic DNA-containing substances. Examples of samples include blood and blood-derived samples such as blood, blood serum, and blood plasma, body fluids such as lymph, sweat, tear, saliva, urine, feces, ascitic fluid, and spinal fluid, and extracts and fractures of cells, tissues and organs. Blood-derived samples are preferably used in the present invention.

Conventional methods in the field of the present invention can be used for hybridization reaction of the amplified nucleic acids obtained by amplification of the template genomic DNA to the nucleic acid probes as well as for measurements of the ratio between the amounts of nucleic acids hybridized to Nucleic Acid Probes a and b, the ratio between the amounts of nucleic acids hybridized to Nucleic Acid Probes c and d, the ratio between the amounts of nucleic acids hybridized to Nucleic Acid Probes e and f, the ratio between the amounts of nucleic acids hybridized to Nucleic Acid Probes a and f, and/or the ratio between the amounts of nucleic acids hybridized to Nucleic Acid Probes e and b. More specifically, they can be performed according to the following procedure.

First, genomic DNA is extracted from the samples obtained from the subjects. Means of DNA extraction preferably may be, without limitation to, a mean which allows direct isolation, purification, and collection of DNA content from the samples described above.

Next, nucleic acid amplification reaction is performed with the template genomic DNA obtained according to the process above to amplify the target region to be detected. Examples of amplification reaction include polymerase chain reaction (PCR) and LAMP (Loop-Mediated Isothermal Amplification). The term "target region to be detected" herein refers to a region which confers a high degree of specificity to allow the detection of polymorphisms in the promoter region of the UGT1A1 gene in the subjects. In the present invention, the target region to be detected comprises a region including at least the TATA box within the promoter region of the UDP-glucuronosyl transferase gene, and more specifically of the UGT1A1 gene.

Furthermore, during amplification of the target region to be detected, it is preferred to attach labels, which subsequently will allow the identification of the amplified nucleic acids. Examples of methods for labeling the amplified nucleic acids herein may be, without limitation to, a method in which the primers used for the nucleic acid amplification reaction are labeled prior to the reaction, or alternatively, a method in which labeled nucleotides are used as the substrates for the nucleic acid amplification reaction. Examples of labels include, without limitation to, radioactive molecules, fluorescent dyes as well as organic compounds such as digoxigenin (DIG) and biotin.

The above described reaction system further includes buffer for nucleic acid amplification and labeling, heat-resistant DNA polymerase, primers specific to the target region to be detected, labeled nucleotide triphosphate, or more specifically fluorescent labeled nucleotide triphosphate, nucleotide triphosphate, and magnesium chloride.

Amplified nucleic acids obtained according to the process above are subsequently hybridized to the nucleic acid probes in the present invention through hybridization reaction. The amount of nucleic acids hybridized to each of the nucleic acid probes can be measured by, for example, label detection. For example, a calibration curve which is obtained by examining samples with known amounts of DNA can be used to determine quantities of amplified nucleic acids hybridized to the nucleic acid probes.

The above described hybridization reaction is preferably performed on a microarray with the carrier-immobilized nucleic acid probes in the present invention, wherein the amplified nucleic acids are applied to the microarray described above. The nucleic acid probes in the present invention (Nucleic Acid Probes a through f) herein can be immobilized to the same carrier or to different carriers. It is preferred to immobilize Nucleic Acid Probes a and b to the same carrier, Nucleic Acid Probes c and d to the same carrier, Nucleic Acid Probes e and f to the same carrier, Nucleic Acid Probes a and f to the same carrier, and Nucleic Acid Probes e and b to the same carrier. All nucleic acid probes (Nucleic Acid Probes a through f) may be immobilized to a single carrier. A plurality of probes for each of Nucleic Acid Probes a through f may be immobilized to a carrier as long as each probe satisfies the respective requirements.

Carrier material for the microarray can be any material which is known in the field of the present invention without limitation. Examples of carrier material includes noble metal such as platinum, platinum black, gold, palladium, rhodium, silver, mercury, tungsten and the compounds thereof, conductive material such as carbon represented by graphite and carbon fiber; silicon material represented by monocrystalline silicon, amorphous silicon, silicon carbide, silicon oxide and silicon nitride, silicon complex material represented by SOI (silicon on insulator); inorganic material such as glass, silica glass, alumina, sapphire, ceramics, forsterite and photosensitive glass; organic material such as polyethylene, ethylene, polypropylene, cyclic polyolefin, polyisobutylene, polyethylene terephthalate, unsaturated polyester, fluorine contained resin, polyvinyl chloride, polyvinylidene chloride, polyvinyl acetate, polyvinyl alcohol, polyvinyl acetal, acrylate resin, polyacrylonitrile, polystyrene, acetal resin, polycarbonate, polyamide, phenol resin, urea resin, epoxy resin, melamine resin, Styrene-Acrylonitrile copolymer, Acrylonitrile-Butadiene-Styrene copolymer, polyphenylene oxide and polysulphone. Not by way of limitation, the carrier is preferably shaped in a tabular configuration.

The carrier for use in the present invention preferably contains a carbon layer and a chemical modification group on its surface. Examples of carrier with a carbon layer as well as a chemical modification group on its surface include a carrier which possess both a carbon layer and a chemical modification group on the surface of the substrate as well as a carrier which possess a chemical modification group on the surface of the substrate consisting of a carbon layer. Substrate material can be any material which is known in the field of the present invention without limitation. The carrier material described above or the like can be employed for substrate.

A carrier which has a refined tabular configuration is used for the preferred embodiment of the present invention. The carrier shapes include but not limited to rectangles, squares and circles. The size of a carrier generally varies from 1 to 75 mm square, preferably 1 to 10 mm square, and more preferably 3 to 5 mm square. It is preferable to use a substrate consisting of silicon material or resin material as it is easy to manufacture it into a carrier in a refined tabular configuration. It is more preferable to use a carrier which has a carbon layer and a chemical modification group on the surface of the substrate consisting of monocrystalline silicon, wherein monocrystalline silicon includes silicon having crystal axes which are slightly tilted in some parts (sometimes described as mosaic crystal) as well as silicon with atomic scale lattice disruption (lattice defect).

The carbon layer to be formed on the surface of the substrate in the present invention can preferably be but not limited to either synthesized diamond, high-pressure synthesized diamond, natural diamond, diamond-like material (such as diamond like carbon), amorphous carbon, or carbonaceous matter (such as graphite, fullerene and carbon nanotube), a mixture thereof or a lamination layer thereof. Other examples include carbide such as hafnium carbide, niobium carbide, silicon carbide, tantalum carbide, thorium carbide, titanium carbide, uranium carbide, tungsten carbide, zirconium carbide, molybdenum carbide, chrome carbide and vanadium carbide. The term "diamond-like material" herein is an umbrella term for imperfect diamond structure consisting of diamond/carbon mixture such as diamond like carbon (DLC), wherein the mixture fraction is not limited. The main advantages of carbon layers can be summarized as follows: carbon layers are chemically stable and can withstand subsequent reactions such as the introduction of chemical modification groups and the binding reaction to the target molecule to be analyzed; carbon layers flexibly bind to the target molecule to be analyzed through electrostatic binding; carbon layers have no absorption in the UV range and thus are transparent to UV, allowing better detection; and carbon layers have good conductive properties, which are beneficial for efficient elecroblotting. Another advantage is that carbon layers have low non-specific absorption during the binding reaction with the target molecule to be analyzed. As mentioned above, a carrier wherein the substrate of the carrier itself consists of a carbon layer may be used if desired.

Formation of the carbon layer in the present invention can be performed by any known method. Examples of methods include microwave plasma CVD (chemical vapor deposit) method, ECRCVD (electric cyclotron resonance chemical vapor deposit) method, ICP (inductive coupled plasma) method, direct-current sputtering technique, ECR (electric cyclotron resonance) sputtering technique, ionized evaporation method, electric arc evaporation method, laser evaporation method, EB (electron beam) evaporation method, and resistance heating evaporation method.

In high-frequency plasma CVD method, raw gas (methane) is decomposed by glow discharge generated between two electrodes due to high frequency to synthesize a DLC (diamond-like carbon) layer on the substrate. In ionized evaporation method, raw gas (benzene) is decomposed and ionized by thermal electron generated by tungsten filament to form a carbon layer on the substrate, using bias voltage. A DLC layer may also be formed by ionized evaporation method in mixed gas comprising 1 to 99 volume percent hydrogen gas and the remaining 99 to 1 volume percent methane gas.

In electric arc evaporation method, arc discharge is generated in vacuum by imposing direct-current voltage between a solid graphite material (cathode evaporation source) and a vacuum vessel (an anode). Plasma of carbon atoms is ejected from the cathode. Carbon ions in the plasma are accelerated towards the substrate by imposing bias voltage which is more negative than the cathodic evaporation source in order to form a carbon layer.

In laser evaporation method, for example, Nd:YAG laser (pulsed laser) beam is used to irradiate and melt a target graphite plate. This allows carbon atoms to be deposited on the surface of the glass substrate to form a carbon layer.

When a carbon layer is formed on the surface of the substrate, the thickness of the carbon layer is generally from the thickness of monolayer to 100 µm. If the carbon layer is too thin, the surface of the underlying substrate may be locally exposed. If the carbon layer is too thick, productivity of carbon layer formation is reduced. Therefore, the thickness of the carbon layer is preferably 2 nm to 1 µm, and more preferably 5 nm to 500 nm.

Nucleic Acid Probes can be strongly immobilized to the carrier by introducing chemical modification groups to the surface of the substrate where the carbon layer is previously formed. Chemical modification groups to be introduced may be arbitrarily determined by one of ordinary skill in the art without being limited. Examples of chemical modification groups include an amino group, a carboxyl group, an epoxy group, a formyl group, a hydroxyl group and an active ester group.

Introduction of an amino group can be carried out, for example, by irradiating ultraviolet rays on the carbon layer in ammonia gas or by plasma treatment of the carbon layer in ammonia gas. Introduction of amino group can also be carried out by irradiating ultraviolet rays on the carbon layer in chlorine gas to chlorinate the same and thereafter irradiating ultraviolet rays on the same in ammonia gas. Alternatively, such introduction can also be carried out by processing a chlorinated carbon layer in the presence of tertiary amine gas such as methylendiamine gas and ethylenediamine gas.

Introduction of a carboxyl group can be carried out, for example, by processing the carbon layer aminated as indicated above with adequate compounds. A compound which can be used to introduce a carboxyl group is exemplified by halocarboxylic acids represented by the general formula X—R1-COOH, in which X is a halogen atom, R1 is a bivalent hydrocarbon group containing 10 to 12 carbon atoms, such as monochloroacetic acid, fluoroacetic acid, bromoacetic acid, iodoacetic acid, 2-chloropropionic acid, 3-chloropropionic acid, 3-chloroacrylate and 4-chlorobenzoic acid; dicarboxylic acids represented by the general formula HOOC—R2-COOH, in which R2 is a single bond or a bivalent hydrocarbon group containing 1 to 12 carbon atoms, such as oxalic acid, malonic acid, succinic acid, maleic acid, fumaric acid and phthalic acid; multivalent carboxylic acids such as polyacrylic acid, polymethacrylic acid, trimellitic acid and butanetetracarboxylic acid; keto acids or aldehyde acids represented by the general formula R3-CO—R4-COOH, in which R3 is a hydrogen atom or a bivalent hydrocarbon group containing 1 to 12 carbon atoms and R4 is a bivalent hydrocarbon group containing 1 to 12 carbon atoms; and dicarboxylic acid monohalides represented by the general formula X—OC—R5-COOH, in which X is a halogen atom and R5 is a single bond or a bivalent hydrocarbon group containing 1 to 12 carbon atoms, such as succinic acid monochloride and malonic acid monochloride; carboxylic acid anhydrides such as phthalic anhydride, succinic anhydride, oxalate anhydride, maleic anhydride and butanetetracarboxylic acid anhydride.

Introduction of an epoxy group can be carried out, for example, by processing the carbon layer aminated as indicated above with adequate multivalent epoxy compounds. Alternatively, such introduction can also be carried out by having carbon-carbon double bonds contained in the carbon layer react with organic peracid. Examples of organic peracids include acetyl hydroperoxide, perbenzoic acid, diperoxy phthalic acid, formyl hydroperoxide and trifluoroperacetic acid.

Introduction of formyl group can be carried out, for example, by processing the carbon layer aminated as indicated above with glutaraldehyde.

Introduction of hydroxyl group can be carried out, for example, by processing the carbon layer chlorinated as indicated above with water.

The term "active ester group" herein refers to any ester group having highly acidic electron withdrawing group on the alcohol side of the ester, rendering the ester activated for nucleophilic reactions. More specifically, active ester can be any ester group with high liability. That is any active ester group having an electron withdrawing group on the alcohol side of the ester and being more activated than alkyl ester. The active ester group demonstrates reactivity to an amino group, a thiol group, and a hydroxyl group. In other words, examples of the active ester group which exhibits significantly higher activity than an alkyl ester include phenol esters, thiophenol esters, N-hydroxyamine esters, cyanomethyl esters and esters of heterocyclic hydroxyl compounds. In more detail, examples of the active ester group include a p-nitrophenyl group, an N-hydroxysuccinimide group, a succinimide group, a phthalic imide group, a 5-norbornene-2,3-dicarboxylmide group. In particular, an N-hydroxysuccineimide group is preferably used.

Introduction of an active ester group can be carried out, for example, by converting a carboxyl group introduced as indicated above to an active ester, using a dehydration-condensation agent such as cyanamide and carbodiimide (for example, 1-[3-(dimethylamino)propyl]-3-ethylcarbodimide and a compound such as N-hydroxysuccineimide. Through this process, a group in which an active ester group such as an N-hydroxysuccineimide group is bound with the end of a hydrocarbon group via an amide bond can be formed (JP Patent Publication (Kokai) No. 2001-139532 A).

The nucleic acid probes in the present invention are dissolved in spotting buffer to prepare a spotting solution. The spotting solution was dispensed into each well of a 96-well or 384-well plastic plate. The dispensed solution is thereafter spotted on the carrier by a spotting apparatus. According to the method above, a microarray with the carrier-immobilized nucleic acid probes can be manufactured. Alternatively, the spotting solution can be manually spotted on the carrier by a micropipetter.

After spotting, incubation is preferably performed to accelerate the binding reaction of the nucleic acid probes to the carrier. The incubation is conducted generally at −20 to +100° C. and preferably at 0 to 90° C., generally for 0.5 to 16 hours and preferably for 1 to 2 hours. The incubation is desirably conducted in a high humidity atmosphere, for example, 50 to 90% humidity. Following the incubation, the carrier is preferably washed in wash solution (for example, 50 mM TBS/ 0.05% Tween20) to remove any nucleic acid unbound to the carrier.

The nucleic acid probes may also be immobilized on the carrier in a plurality of spots with incremental amounts of immobilized DNA. For example, a plurality of spots carrying 1 ng, 100 pg and 10 pg of DNA can be formed for each nucleic acid probe. This allows semiquantitation of the target region to be detected.

Furthermore, the present invention relates to a kit used to determine the genotypes of the UDP-glucuronosyl transferase gene (UGT1A1 gene), wherein the kit includes at least one of the nucleic acid probe pairs selected from the group consisting Nucleic Acid Probes a and b, c and d, e and f, a and f, and e and b of the present invention. More specifically, the present invention relates to a kit used to determine the risk of adverse effects of irinotecan in a subject. Nucleic Acid Probes (Nucleic Acid Probes a through f) for the kit in the present invention may be provided in the form of a microarray, wherein the nucleic acid probes are immobilized to the carrier. Furthermore, the kit in the present invention may include buffer for nucleic acid amplification and labeling, heat-resistant DNA polymerase, primers specific to the target region to be detected, labeled nucleotide triphosphate, or more specifically fluorescent labeled nucleotide triphosphate, nucleotide triphosphate, and magnesium chloride. Primers specific to the target region to be detected are preferably primers used to amplify the region which includes at least the TATA box within the promoter region of the UGT1A1 gene.

DETAILED DESCRIPTION OF THE PREFERRED EMBODIMENTS

Example 1

Examination of Nucleotide Length of Nucleic Acid Probes 1-1. Manufacture of Carrier A two-layer diamond like carbon (DLC) was formed on a 3 mm square silicon substrate by an ionized evaporation method under the conditions described hereinafter.

TABLE 1

|  |  | First layer | Second layer |  |
| --- | --- | --- | --- | --- |
| Raw gas | $CH_4$ | 4.75 | 47.5 | (sccm) |
|  | $H_2$ | 0.25 | 2.5 | (sccm) |
| Working pressure |  | 3.0 | 8.0 | (Pa) |
| Substrate bias | Direct-current voltage | 500 | 500 | (V) |
|  | High frequency output | 100 | — | (W) |
| Anode voltage |  | 50 | 50 | (V) |
| Filament | Voltage | 7 | 7 | (V) |
|  | Current | 22 | 22 | (A) |

An amino group was introduced to the obtained silicon substrate having a DLC layer on its surface, using ammonia plasma under the conditions described hereinafter.

TABLE 2

| Raw gas | $NH_3$ | 30 | (sccm) |
| --- | --- | --- | --- |
| Working pressure |  | 8.0 | (Pa) |
| Substrate bias | Direct-current voltage | 500 | (V) |
|  | High frequency output | — | (W) |
| Anode voltage |  | 50 | (V) |
| Filament | Voltage | 7 | (V) |
|  | Current | 22 | (A) |

A carboxyl group was subsequently introduced to the substrate by a 30-minute immersion in a solution containing 1-methyl-2-pyrolidone, 140 mM succinic anhydride and 0.1 M sodium borate. Activation reaction was performed by a 30-minute immersion in a solution containing 0.1 M potassium phosphate buffer, 0.1 M 1-[3-(dimethylamino)propyl]-3-ethylcarbodiimide and 20 mM N-hydroxysuccinimide. This yielded a carrier consisting of a silicon substrate with a surface having a DLC layer as well as N-hydroxysuccinimide group as a chemical modification group.

1-2. Synthesis of Nucleic Acid Probes

Nucleic Acid Probes which contained the partial sequences including at least the TATA box within the promoter region of the UDP-glucuronosyl transferase gene (UGT1A1) with 6 or 7 TA repeats in the TATA box, wherein the nucleotide length of each of the nucleic acid probes was either 20 mer, 30 mer or 50 mer, were synthesized.

The nucleotide sequences of the synthesized nucleic acid probes are described hereinafter.

```
50 mer
Probe 1 (TA x 7):
                                       (SEQ ID NO: 11)
5'-GTATCGATTGGTTTTTGCCATATATATATATATATAAGTAGGAGAGG

GCG-3'

Probe 2 (TA x 6):
                                       (SEQ ID NO: 12)
5'-TGTATCGATTGGTTTTTGCCATATATATATATATAAGTAGGAGAGGG

CGA-3'

30 mer
Probe 3 (TA x 7):
                                       (SEQ ID NO: 3)
5'-TTTTGCCATATATATATATATATAAGTAGG-3'

Probe 4 (TA x 6):
                                       (SEQ ID NO: 4)
5'-TTTTGCCATATATATATATATAAGTAGGAG-3'

20 mer
Probe 5 (TA x 7):
                                       (SEQ ID NO: 13)
5'-GCCATATATATATATATATA-3'

Probe 6 (TA x 6):
                                       (SEQ ID NO: 14)
5'-TTGCCATATATATATATATA-3'
```

1-3. Immobilization of Nucleic Acid Probes

A 10 μM Solution of each nucleic acid probe synthesized according to Step 1-2 was spotted onto the carrier manufactured according to Step 1-1. After spotting, the carrier was incubated at 80° C. for 1 hour, washed in 2×SSC/0.2% SDS solution, and dried to manufacture a microarray.

1-4. Preparation of Target DNA

Genomic DNAs isolated from the blood samples (Samples 1 to 3) obtained from subjects with different genotypes were used as templates for PCR reactions using fluorescent labeled nucleotides to prepare fluorescent labeled target DNAs (amplified nucleic acids). The primers used for the PCR reactions are described hereinafter.

```
Forward primer:
5'-CCTTCTTCCTCTCTGGTAACAC-3'    (SEQ ID NO: 15)

Reverse primer:
5'-CGTCAGGTGCTAGGACAACTAT-3'    (SEQ ID NO: 16)
```

Sample 1 was a blood sample obtained from a subject whose genotype was wild-type (designated as TA6/TA6) with 2 wild-type alleles having 6 TA repeats in the TATA box (designated as TA6). Sample 2 was a blood sample obtained from a subject whose genotype was heterozygous variant type (designated as TA6/TA7), carrying one variant allele with 7 repeats (designated as TA7) and one wild-type allele described above. Sample 3 was a blood sample obtained from a subject whose genotype was homozygous variant type (designated as TA7/TA7), carrying two variant allele described above.

Conditions for the PCR reactions are described hereinafter.

TABLE 3

| Reaction solution | |
|---|---|
| Primer FW (10 pmol/μl) | 1 μl |
| Primer RV (10 pmol/μl) | 1 μl |
| dNTP Mix (2.5 μl, dCTP 1/10 concentration) | 2 μl |
| 1 mM Cy5-dCTP | 0.5 μl |
| 10 × PCR buffer | 2 μl |
| Genome Template (3 ng/μl) | 1 μl |
| H$_2$O | 13 μl |
| EX Taq Polymerase (Takara) | 0.1 μl |
| Total | 20 μl |
| Reaction cycle | |
| Thermal denaturation | 94° C., 10 sec |
| Annealing | 55° C., 10 sec  ] 35 cycles |
| Elongation reaction | 72° C., 10 sec |

1-5. Hybridization

A hybridization solution (4×SSC solution) containing the target DNA was prepared. Hybridization reaction was performed by immersing the microarray manufactured according to Example 1 in 25 μl of the hybridization solution at 50° C. for 2 hours. After washing, the microarray was inserted to a fluorescent scanner (FLA8000/Fuji Film) for obtaining fluorescent images (FIG. 1).

1-6. Analysis Estimate

Figure 2:
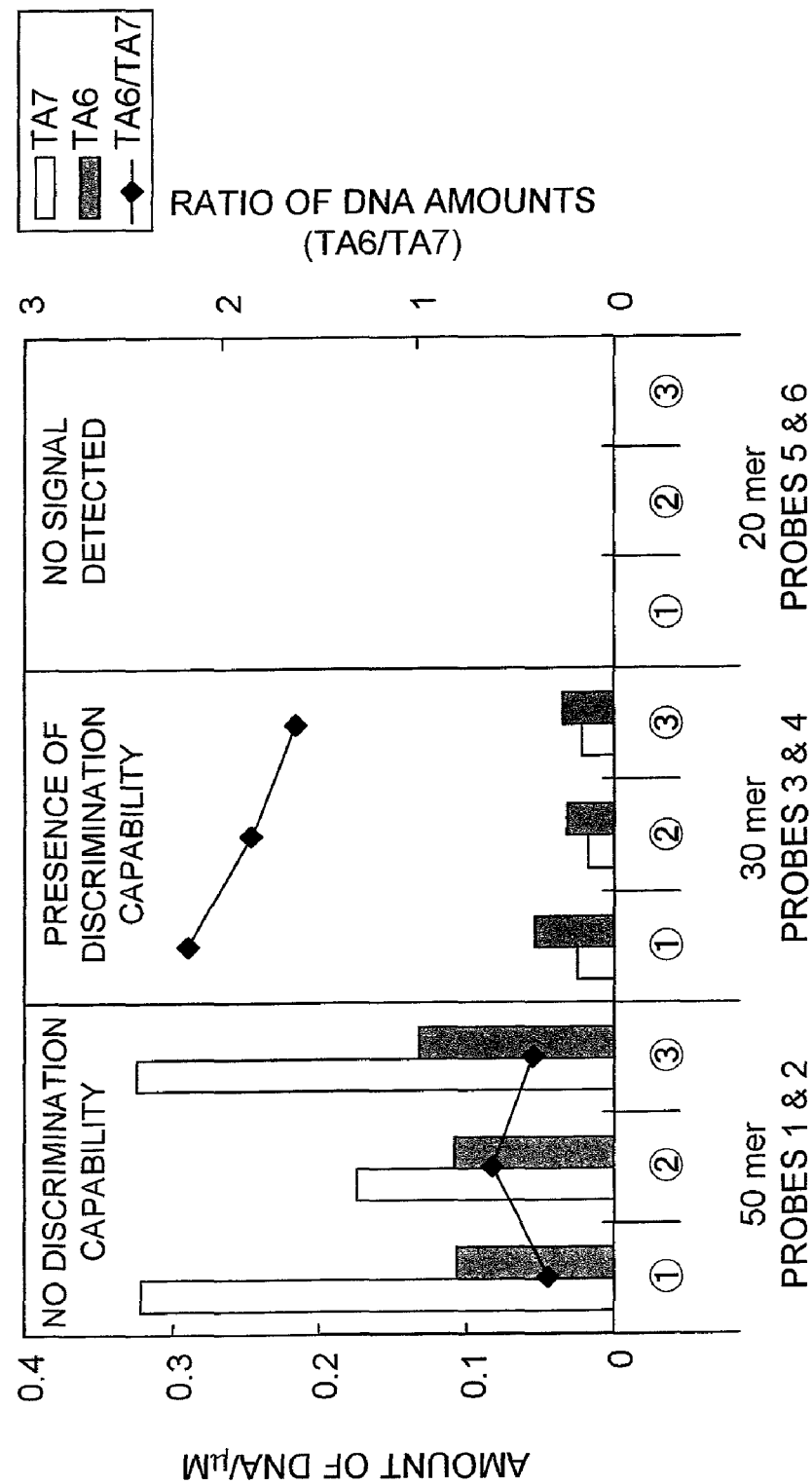
FIG. 2 is a graph showing the DNA content converted from fluorescence intensity of the spot where each probe is immobilized, analyzing the fluorescence images of FIG. 1. The bars for each sample represent the amount of DNA hybridized to the probe comprising 6 TA repeats (TA6) as well as the amount of DNA hybridized to the probe comprising 7 TA repeats (TA7). The line plot represents the ratio (TA6/TA7) between the amount of DNA hybridized to the probe comprising 6 TA repeats (TA6) and the amount of DNA hybridized to the probe comprising 7 TA repeats (TA7)

Fluorescence image analysis was performed in Genepix-Pro (Axon) to measure the fluorescence intensity of the spot where each probe was immobilized. A calibration curve for DNA concentration and fluorescence intensity was obtained. The calibration curve was used to convert the fluorescence intensities of the spots into quantities of DNAs (μM). Results are shown in FIG. 2. The bars for each sample represent the amount of DNA hybridized to the probe containing 6 TA repeats (TA6) as well as the amount of DNA hybridized to the probe containing 7 TA repeats (TA7). The line plot represents the ratio (TA6/TA7) between the amount of DNA hybridized to the probe containing 6 TA repeats (TA6) and the amount of DNA hybridized to the probe containing 7 TA repeats (TA7).

Results shown in FIG. 2 indicate that a combination of the 30 mer probes which have 6 or 7 TA repeats respectively allowed the detection of polymorphisms in the promoter region of the UDP-glucuronosyl transferase gene in the subjects by measuring the ratio between the amounts of DNAs hybridized to the probes. As homozygous variant type (TA7/TA7) is the most risk genotype, followed by (in descending order) heterozygous variant type (TA6/TA7), followed by (in descending order) the wild-type (TA6/TA6) in terms of the risk of adverse effects of irinotecan, it was demonstrated that the risk of adverse effects of irinotecan could be detected by detecting polymorphisms in the promoter region of the UDP-glucuronosyl transferase gene with the use of the probes in the present invention.

In contrast, the 50 mer probes failed to determine the genotype of each sample due to a high non-specific signal in the samples, although the fluorescent intensities obtained using the 50 mer probes were high. No fluorescence signal was detected from the 20 mer probes.

Example 2

Examination of Nucleic Acid Probe Sequence 2-1. Manufacture of Microarray

A carrier consisting of a silicon substrate with a surface having a DLC layer as well as an N-hydroxysuccinimide group as a chemical modification group was manufactured in the same manner as in Step 1-1 of Example 1.

In Example 1, the 30 mer probes offered the highest accuracy in detecting the polymorphisms. For this reason, nucleic acid probes which contained the partial sequences including at least the TATA box within the promoter region of the UDP-glucuronosyl transferase gene (UGT1A1 gene) with 6 or 7 TA repeats in the TATA box, wherein each of the nucleic acid probes consisted of a 30 mer nucleotide sequence different from Probes 3 and 4 or the nucleic acid probes consisted of a nucleotide sequence complementary to the sequence of Probes 3 or 4, were synthesized.

The nucleotide sequences of the nucleic acid probes synthesized are described hereinafter.

Different Sets of 30 mer Partial Sequences

```
Probe 7 (TA x 7):
5'-ATTGGTTTTTGCCATATATATATATATATA-3' (SEQ ID NO: 5)

Probe 8 (TA x 6):
5'-CGATTGGTTTTTGCCATATATATATATATA-3' (SEQ ID NO: 6)

Complementary sequences
Probe 9 (TA x 7):
5'-CCTACTTATATATATATATATATGGCAAAA-3' (SEQ ID NO: 7)

Probe 10 (TA x 7):
5'-CTCCTACTTATATATATATATATGGCAAAA-3' (SEQ ID NO: 8)
```

A microarray was manufactured by spotting 10 μM solution of each of the nucleic acid probes synthesized onto the carrier in the same manner as in Step 1-3 of Example 1.

2-2. Detection of Polymorphisms

Figure 3:
FIG. 3 shows the position of each nucleic acid probe spot on a microarray manufactured according to Example 2 as well as fluorescence images of the amplified nucleic acids hybridized to the microarray, taken with a fluorescence scanner.

A hybridization solution (4×SSC solution) containing the target DNA obtained according to Step 1-4 in Example 1 was prepared. Hybridization reaction was performed by immersing the microarray manufactured according to Step 2-1 described above in 25 μl of the hybridization solution at 50° C. for 2 hours. After washing, the microarray was inserted to a fluorescent scanner (FLA8000/Fuji Film) for obtaining fluorescent images (FIG. 3).

Fluorescence image analysis was performed in Genepix-Pro (Axon) to measure the fluorescence intensity of the spot where each probe was immobilized. A calibration curve for DNA concentration and fluorescence intensity was obtained. The calibration curve was used to convert the fluorescence intensities of the spots into quantities of DNAs (μM). Results are shown in FIG. 4.

The bars for each sample represent the amount of DNA hybridized to the probe containing 6 TA repeats (TA6) as well as the amount of DNA hybridized to the probe containing 7 TA repeats (TA7). The line plot represents the ratio (TA6/TA7) between the amount of DNA hybridized to the probe containing 6 TA repeats (TA6) and the amount of DNA hybridized to the probe containing 7 TA repeats (TA7).

Figure 4:
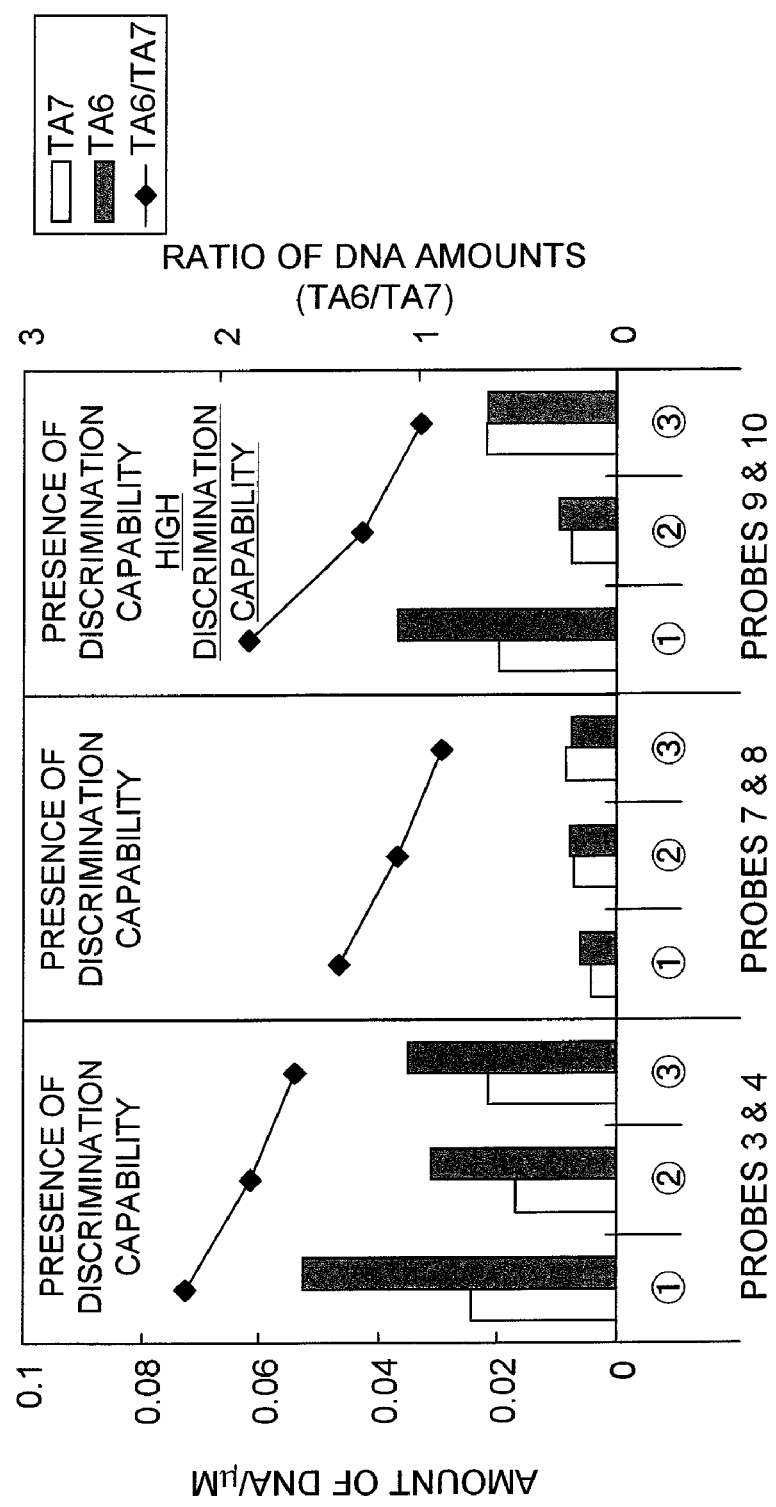
FIG. 4 is a graph showing the DNA content converted from fluorescence intensity of the spot where each probe is immobilized, analyzing the fluorescence images of FIG. 3. The bars for each sample represent the amount of DNA hybridized to the probe comprising 6 TA repeats (TA6) as well as the amount of DNA hybridized to the probe comprising 7 TA repeats (TA7). The line plot represents the ratio (TA6/TA7) between the amount of DNA hybridized to the probe comprising 6 TA repeats (TA6) and the amount of DNA hybridized to the probe comprising 7 TA repeats (TA7)

Results shown in FIG. 4 indicate that any combination of the 30 mer probes synthesized according to the present embodiment allowed the detection of polymorphisms in the promoter region of the UDP-glucuronosyl transferase gene (UGT1A1 gene) in the subjects by measuring the ratio between the amount of DNA hybridized to the probe containing 6 TA repeats and the amount of DNA hybridized to the probe containing 7 TA repeats.

Furthermore, Probes 7 and 8 showed a decrease in signal intensity, compared with Probe 3 and 4. In contrast, Probes 9 and 10, which corresponded to the complementary strands of Probes 3 and 4, offered an increased accuracy in determining the genotypes based on the amount of DNA hybridized due to reduced non-specific signals although they showed a slight decrease in signal intensity.

Example 3

Examination of Repeat Sequence of Nucleic Acid Probes 3-1. Manufacture of Microarray A carrier consisting of a silicon substrate with a surface having a DLC layer as well as N-hydroxysuccinimide group as a chemical modification group was manufactured in the same manner as in Step 1-1 of Example 1.

In Example 1, the 30 mer probes offered the highest accuracy in detecting polymorphisms. For this reason, nucleic acid probes which contained the partial sequences including at least the TATA box within the promoter region of the UDP-glucuronosyl transferase gene (UGT1A1 gene), wherein the nucleic acid probes were designed to have 8 nucleotides between the end of the TATA box and the 3' end, wherein each of the nucleic acid probes furthermore contained 6 or 7, and 5 or 8 TA repeats in the TATA box, were synthesized.

The nucleotide sequences of nucleic acid probes synthesized are described hereinafter. Nucleotide sequences with 6 or 7 TA repeats

```
Probe 3 (TA x 7):
5'-TTTTGCCATATATATATATATATATAAGTAGG-3' (SEQ ID NO: 3)

Probe 11 (TA x 6):
5'-GTTTTTGCCATATATATATATATATAAGTAGG-3' (SEQ ID NO: 17)

Nucleotide sequences with 5 or 8 TA repeats
Probe 12 (TA x 8):
5'-TTGCCATATATATATATATATATATAAGTAGG-3' (SEQ ID NO: 18)

Probe 13 (TA x 5):
5'-TGGTTTTTGCCATATATATATATAAGTAGG-3' (SEQ ID NO: 19)
```

A microarray was manufactured by spotting 10 µM solution of each of the nucleic acid probes synthesized onto the carrier in the same manner as in Step 1-3 of Example 1.

3-2. Detection of Polymorphisms

Hybridization solution (4×SSC solution) containing the target DNA obtained according to Step 1-4 in Example 1 was prepared. Hybridization reaction was performed by immersing the microarray manufactured according to Step 3-1 described above in 25 µl of the hybridization solution at 50° C. for 2 hours. After washing, the microarray was inserted to a fluorescent scanner (FLA8000/Fuji Film) for obtaining fluorescent images (FIG. 5).

Fluorescence image analysis was performed in Genepix-Pro (Axon) to measure the fluorescence intensity of the spot where each probe was immobilized. A calibration curve for DNA concentration and fluorescence intensity was obtained. The calibration curve was used to convert the fluorescence intensities of the spots into quantities of DNAs (µM). Results are shown in FIG. 6.

The bars for each sample represent the amount of DNA hybridized to the probe containing 6 TA repeats (TA6) and the amount of DNA hybridized to the probe containing 7 TA repeats (TA7) as well as the amount of DNA hybridized to the probe containing 5 TA repeats (TA5) and the amount of DNA hybridized to the probe containing 8 TA repeats (TA8). The line plots represent the ratio (TA6/TA7) between the amount of DNA hybridized to the probe containing 6 TA repeats and the amount of DNA hybridized to the probe containing 7 TA repeats as well as the ratio (TA5/TA8) between the amount of DNA hybridized to the probe containing 5 TA repeats and the amount of DNA hybridized to the probe containing 8 TA repeats.

Figure 6:
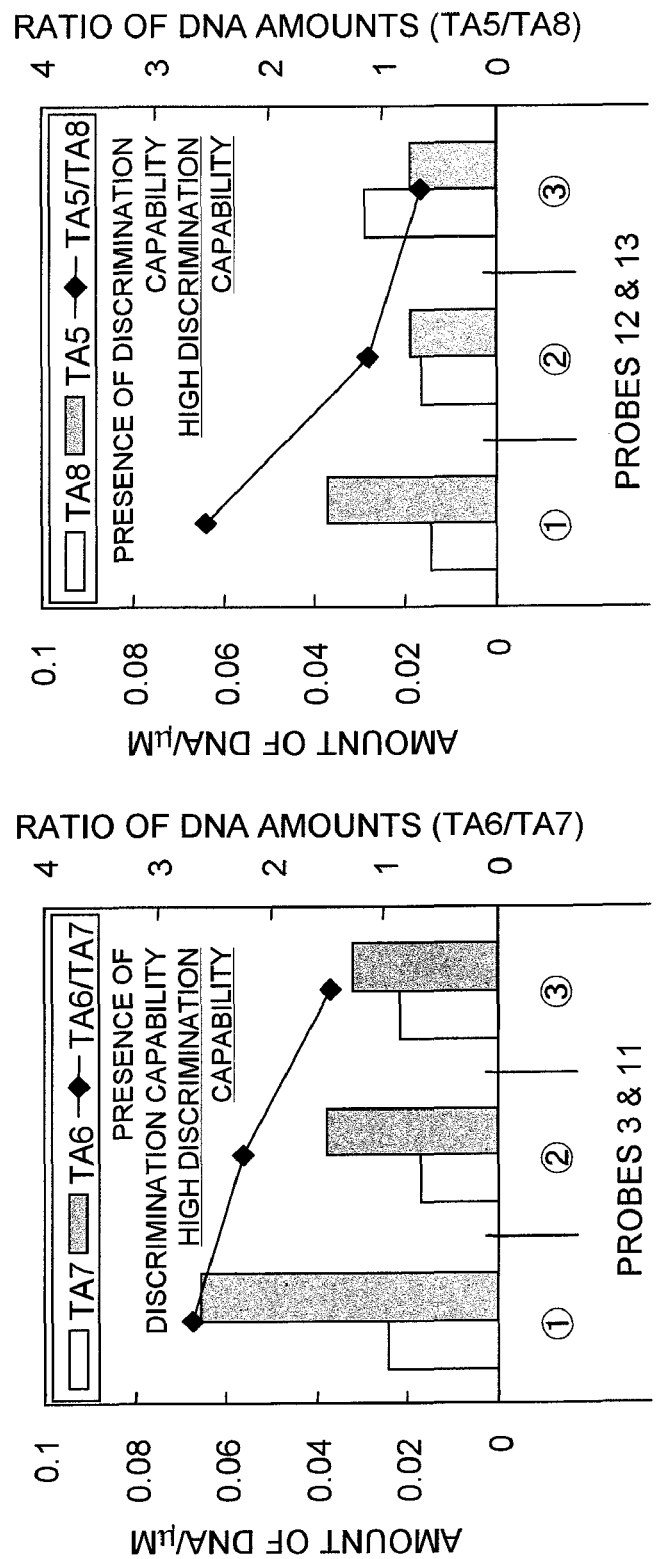
FIG. 6 is a graph showing the DNA content converted from fluorescence intensity of the spot where each probe is immobilized, analyzing the fluorescence images of FIG. 5. The bars for each sample represent the amount of DNA hybridized to the probe comprising 6 TA repeats (TA6) as well as the amount of DNA hybridized to the probe comprising 7 TA repeats (TA7), and the amount of DNA hybridized to the probe comprising 5 TA repeats (TA5) as well as the amount of DNA hybridized to the probe comprising 8 TA repeats (TA8). The line plots represent the ratio (TA6/TA7) between the amount of DNA hybridized to the probe comprising 6 TA repeats and the amount of DNA hybridized to the probe comprising 7 TA repeats as well as the ratio (TA5/TA8) between the amount of DNA hybridized to the probe comprising 5 TA repeats and the amount of DNA hybridized to the probe comprising 8 TA repeats.

Results shown in FIG. 6 indicate that any combination of the 30 mer probes synthesized according to the present embodiment allowed the detection of polymorphisms in the promoter region of the UDP-glucuronosyl transferase gene (UGT1A1 gene) in the subjects by measuring the ratio between the amount of DNA hybridized to the probe containing 6 TA repeats and the amount of DNA hybridized to the probe containing 7 TA repeats as well as the ratio between the amount of DNA hybridized to the probe containing 5 TA repeats and the amount of DNA hybridized to the probe containing 8 TA repeats.

Furthermore, the probes which were designed to have 8 nucleotides between the end of the TATA box and the 3' end offered an increased accuracy in determining the genotypes due to reduced non-specific signals.

All references, including any publications, patents or patent applications cited in this specification are hereby incorporated by reference in their entirely.

What is claimed is:

1. A method for determining the risk of adverse effects of irinotecan comprising:
   amplifying a target region of a nucleic acid sample obtained from a subject at risk of experiencing adverse effects of irinotecan, wherein said target region comprises the TATA box within the promoter region of the UDP glucuronosyl transferase (UGT1A1) gene;
   hybridizing to the amplified nucleic acid at least one pair of nucleic acid probes selected from the group of probes a and b, c and d, e and f, a and f, and e and b,
   measuring the ratio between the amount of nucleic acid hybridized to each individual probe in a pair of probes a/b, c/d, and e/f; and
   determining a lower risk of adverse effects to irinotecan when the ratio of b/a, d/c, f/e, f/a, b/e is high compared to a subject having a lower ratio;
   wherein said method comprises:
   hybridizing the nucleic acid probe pair a and b; wherein probe a consists of the nucleotide sequence of SEQ ID NO: 3 and probe b consists of the nucleotide sequence of either SEQ ID NO: 4 or NO: 17, or alternatively probe a consists of the nucleotide sequence of SEQ ID NO: 5 and probe b consists of the nucleotide sequence of SEQ ID NO: 6;
   hybridizing the nucleic acid probe pair c and d; wherein probe c consists of the nucleotide sequence of SEQ ID NO: 7 and probe d consists of the nucleotide sequence of SEQ ID NO: 8, or alternatively probe c consists of the nucleotide sequence of SEQ ID NO: 9 and probe d consists of the nucleotide sequence of SEQ ID NO: 10;
   hybridizing the nucleic acid probe pair e and f; wherein probe e consists of the nucleotide sequence of SEQ ID NO: 18 and probe f consists of the nucleotide sequence of SEQ ID NO: 19;
   hybridizing the nucleic acid probe pair a and b; wherein probe a consists of the nucleotide sequence of SEQ ID NO: 3 with one or two-nucleotide deletion at its 3' and/or 5' end and probe b consists of the nucleotide sequence of either SEQ ID NO: 4 or NO: 17 with one or two-nucleotide deletion at its 3' and/or 5' end, or alternatively probe a consists of the nucleotide sequence of SEQ ID NO: 5 with one or two-nucleotide deletion at its 3' and/or 5' end and probe b consists of the nucleotide sequence of SEQ ID NO:6 with one or two-nucleotide deletion at its 3' and/or 5' end;
   hybridizing the nucleic acid probe pair c and d; wherein c consists of the nucleotide sequence of SEQ ID NO: 7 with one or two-nucleotide deletion at its 3' and/or 5' end and probe d consists of the nucleotide sequence of SEQ ID NO: 8 with one or two-nucleotide deletion at its 3' and/or 5' end, or alternatively probe c consists of the nucleotide sequence of SEQ ID NO: 9 with one or two-nucleotide deletion at its 3' and/or 5' end and probe d consists of the nucleotide sequence of SEQ ID NO: 10 with one or two-nucleotide deletion at its 3' and/or 5' end; or
   hybridizing the nucleic acid probe pair e and f; wherein probe e consists of the nucleotide sequence of SEQ ID NO: 18 with one or two-nucleotide deletion at its 3' and/or 5' end and probe f consists of the nucleotide sequence of SEQ ID NO: 19 with one or two-nucleotide deletion at its 3' and/or 5' end.

2. The method of claim 1 comprising:
   (1) amplifying a region comprising the TATA box within the promoter region of the UDP-glucuronosyl transferase gene, using its template genomic DNA isolated from a sample obtained from a subject;
   (2) hybridizing the amplified nucleic acids obtained in (1) to at least one of the nucleic acid probe pairs selected from the group consisting of probes a and b, c and d, and e and f; and
   (3) measuring the ratio between the amount of nucleic acids hybridized to probe a and the amount of nucleic acids hybridized to probe b, the ratio between the amount of nucleic acids hybridized to probe c and the amount of nucleic acids hybridized to probe d, or the ratio between the amount of nucleic acids hybridized to probe e and the amount of nucleic acids hybridized to probe f.

3. The method of claim 1, which comprises hybridizing the nucleic acid probe pair a and b; wherein
   probe a consists of the nucleotide sequence of SEQ ID NO: 3 and probe b consists of the nucleotide sequence of either SEQ ID NO: 4 or NO: 17, or alternatively
   probe a consists of the nucleotide sequence of SEQ ID NO: 5 and probe b consists of the nucleotide sequence of SEQ ID NO: 6.

4. The method of claim 1, which comprises hybridizing the nucleic acid probe pair c and d; wherein
   probe c consists of the nucleotide sequence of SEQ ID NO: 7 and probe d consists of the nucleotide sequence of SEQ ID NO: 8, or alternatively probe c consists of the nucleotide sequence of SEQ ID NO: 9 and probe d consists of the nucleotide sequence of SEQ ID NO: 10.

5. The method of claim 1, which comprises hybridizing the nucleic acid probe pair e and f; wherein
probe e consists of the nucleotide sequence of SEQ ID NO: 18 and probe f consists of the nucleotide sequence of SEQ ID NO: 19.

6. The method of claim 1, which comprises hybridizing the nucleic acid probe pair a and b;
wherein probe a consists of the nucleotide sequence of SEQ ID NO: 3 with one or two-nucleotide deletion at its 3' and/or 5' end and probe b consists of the nucleotide sequence of either SEQ ID NO: 4 or NO: 17 with one or two-nucleotide deletion at its 3' and/or 5' end, or alternatively
probe a consists of the nucleotide sequence of SEQ ID NO: 5 with one or two-nucleotide deletion at its 3' and/or 5' end and probe b consists of the nucleotide sequence of SEQ ID NO:6 with one or two-nucleotide deletion at its 3' and/or 5' end.

7. The method of claim 1, which comprises hybridizing the nucleic acid probe pair c and d;
wherein c consists of the nucleotide sequence of SEQ ID NO: 7 with one or two-nucleotide deletion at its 3' and/or 5' end and probe d consists of the nucleotide sequence of SEQ ID NO: 8 with one or two-nucleotide deletion at its 3' and/or 5' end, or alternatively
probe c consists of the nucleotide sequence of SEQ ID NO: 9 with one or two-nucleotide deletion at its 3' and/or 5' end and probe d consists of the nucleotide sequence of SEQ ID NO: 10 with one or two-nucleotide deletion at its 3' and/or 5' end.

8. The method of claim 1, which comprises hybridizing the nucleic acid probe pair e and f;
wherein probe e consists of the nucleotide sequence of SEQ ID NO: 18 with one or two-nucleotide deletion at its 3' and/or 5' end and probe f consists of the nucleotide sequence of SEQ ID NO: 19 with one or two-nucleotide deletion at its 3' and/or 5' end.

9. A kit used to detect the adverse effects of irinotecan, which comprises at least one of the nucleic acid probe pairs selected from the group consisting of probes a and b, c and d, and e and f; provided that
when said pair is a and b, then probe a consists of the nucleotide sequence of SEQ ID NO: 3 and probe b consists of the nucleotide sequence of either SEQ ID NO: 4 or NO: 17; probe a consists of the nucleotide sequence of SEQ ID NO: 5 and probe b consists of the nucleotide sequence of SEQ ID NO: 6; probe a consists of the nucleotide sequence of SEQ ID NO: 3 with one or two-nucleotide deletion at its 3' and/or 5' end and probe b consists of the nucleotide sequence of either SEQ ID NO: 4 or NO: 17 with one or two-nucleotide deletion at its 3' and/or 5' end; or probe a consists of the nucleotide sequence of SEQ ID NO: 5 with one or two-nucleotide deletion at its 3' and/or 5' end and probe b consists of the nucleotide sequence of SEQ ID NO: 6 with one or two-nucleotide deletion at its 3' and/or 5' end;
when said pair is c and d, then probe c consists of the nucleotide sequence of SEQ ID NO: 7 and probe d consists of the nucleotide sequence of SEQ ID NO: 8, or alternatively probe c consists of the nucleotide sequence of SEQ ID NO: 9 and probe d consists of the nucleotide sequence of SEQ ID NO: 10; probe c consists of the nucleotide sequence of SEQ ID NO: 7 with one or two-nucleotide deletion at its 3' and/or 5' end and probe d consists of the nucleotide sequence of SEQ ID NO: 8 with one or two-nucleotide deletion at its 3' and/or 5' end; or alternatively probe c consists of the nucleotide sequence of SEQ ID NO: 9 with one or two-nucleotide deletion at its 3' and/or 5' end and probe d consists of the nucleotide sequence of SEQ ID NO: 10 with one or two-nucleotide deletion at its 3' and/or 5' end;
when said pair is e and f, then probe e consists of the nucleotide sequence of SEQ ID NO: 18 and probe f consists of the nucleotide sequence of SEQ ID NO: 19; or probe e consists of the nucleotide sequence of SEQ ID NO: 18 with one or two-nucleotide deletion at its 3' and/or 5' end and probe f consists of the nucleotide sequence of SEQ ID NO: 19 with one or two-nucleotide deletion at its 3' and/or 5' end.

10. The kit of claim 9, comprising a microarray wherein said one or more pairs of nucleic acid probes are immobilized on a carrier.

11. The kit of claim 9, comprising pair a and b, wherein
probe a consists of the nucleotide sequence of SEQ ID NO: 3 and probe b consists of the nucleotide sequence of either SEQ ID NO: 4 or NO: 17, or alternatively
probe a consists of the nucleotide sequence of SEQ ID NO: 5 and probe b consists of the nucleotide sequence of SEQ ID NO: 6.

12. The kit of claim 9, comprising pair c and d, wherein
probe c consists of the nucleotide sequence of SEQ ID NO: 7 and probe d consists of the nucleotide sequence of SEQ ID NO: 8, or alternatively
probe c consists of the nucleotide sequence of SEQ ID NO: 9 and probe d consists of the nucleotide sequence of SEQ ID NO: 10.

13. The kit of claim 9, comprising pair e and f, wherein
probe e consists of the nucleotide sequence of SEQ ID NO: 18 and probe f consists of the nucleotide sequence of SEQ ID NO: 19.

14. The kit of claim 9, comprising pair a and b, wherein
probe a consists of the nucleotide sequence of SEQ ID NO: 3 with one or two-nucleotide deletion at its 3' and/or 5' end and probe b consists of the nucleotide sequence of either SEQ ID NO: 4 or NO: 17 with one or two-nucleotide deletion at its 3' and/or 5' end, or alternatively
probe a consists of the nucleotide sequence of SEQ ID NO: 5 with one or two-nucleotide deletion at its 3' and/or 5' end and probe b consists of the nucleotide sequence of SEQ ID NO: 6 with one or two-nucleotide deletion at its 3' and/or 5' end.

15. The kit of claim 9, comprising pair c and d, wherein
probe c consists of the nucleotide sequence of SEQ ID NO: 7 with one or two-nucleotide deletion at its 3' and/or 5' end and probe d consists of the nucleotide sequence of SEQ ID NO: 8 with one or two-nucleotide deletion at its 3' and/or 5' end, or alternatively
probe c consists of the nucleotide sequence of SEQ ID NO: 9 with one or two-nucleotide deletion at its 3' and/or 5' end and probe d consists of the nucleotide sequence of SEQ ID NO: 10 with one or two-nucleotide deletion at its 3' and/or 5' end.

16. The kit of claim 9, comprising pair e and f, wherein
probe e consists of the nucleotide sequence of SEQ ID NO: 18 with one or two-nucleotide deletion at its 3' and/or 5' end and probe f consists of the nucleotide sequence of SEQ ID NO: 19 with one or two-nucleotide deletion at its 3' and/or 5' end.

* * * * *

SEQUENCE LISTING

```
<160> NUMBER OF SEQ ID NOS: 19

<210> SEQ ID NO 1
<211> LENGTH: 492
<212> TYPE: DNA
<213> ORGANISM: Homo sapiens

<400> SEQUENCE: 1
caagtgagca ggcagtaccg ggggagctgt ggagtgggca ctcttacagg tttccatggc      60
gaaagcgggg gtacagttgt gttctttttct ttctaaaagg ctttctaaaa agccttctgt    120 ttaattttg gaaaagaagc ctaacttgtt cactacatag tcgtccttct tcctctctgg     180
```

```
taacacttgt tggtctgtgg aaatactaat ttaatggatc ctgaggttct ggaagtactt    240
tgctgtgttc actcaagaat gtgatttgag tatgaaattc cagccagttc aactgttgtt    300
gcctattaag aaacctaata aagctccacc ttctttatct ctgaaagtga actccctgct    360
acctttgtgg actgacagct ttttatagtc acgtgacaca gtcaaacatt aacttggtgt    420
atcgattggt ttttgccata tatatatata tataagtagg agagggcgaa cctctggcag    480
gagcaaaggc gc                                                       492

<210> SEQ ID NO 2
<211> LENGTH: 490
<212> TYPE: DNA
<213> ORGANISM: Homo sapiens

<400> SEQUENCE: 2
caagtgagca ggcagtaccg ggggagctgt ggagtgggca ctcttacagg tttccatggc     60
gaaagcgggg gtacagttgt gttctttttct ttctaaaagg cttctaaaa agccttctgt    120 ttaatttctg gaaagaagc ctaacttgtt cactacatag tcgtccttct tcctctctgg    180
taacacttgt tggtctgtgg aaatactaat ttaatggatc ctgaggttct ggaagtactt    240
tgctgtgttc actcaagaat gtgatttgag tatgaaattc cagccagttc aactgttgtt    300
gcctattaag aaacctaata aagctccacc ttctttatct ctgaaagtga actccctgct    360
acctttgtgg actgacagct ttttatagtc acgtgacaca gtcaaacatt aacttggtgt    420
atcgattggt ttttgccata tatatata taagtaggag agggcgaacc tctggcagga    480
gcaaaggcgc                                                          490

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ttttgccata tatatata tataagtagg                                       30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ttttgccata tatatata taagtaggag                                       30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
attggttttt gccatatata tatatatata                                     30

<210> SEQ ID NO 6
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
cgattggttt ttgccatata tatatatata                                      30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
cctacttata tatatatata tatggcaaaa                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ctcctactta tatatatata tatggcaaaa                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
tatatatata tatatatggc aaaaaccaat                                      30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
tatatatata tatggcaa aaaccaatcg                                        30

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gtatcgattg gttttttgcca tatatatata tataagta ggagagggcg                 50

<210> SEQ ID NO 12
<211> LENGTH: 50
<212> TYPE: DNA
```

<213> ORGANISM: Artificial Sequence
<220> FEATURE:
<223> OTHER INFORMATION: Description of Artificial Sequence: Synthetic
      DNA

<400> SEQUENCE: 12
tgtatcgatt ggtttttgcc atatatatat atataagtag gagagggcga          50

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
gccatatata tatatatata                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
ttgccatata tatatatata                                           20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
ccttcttcct ctctggtaac ac                                        22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
cgtcaggtgc taggacaact at                                        22

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
gtttttgcca tatatatata tataagtagg                                30

<210> SEQ ID NO 18
<211> LENGTH: 30
<212> TYPE: DNA
<213> ORGANISM: Artificial Sequence
<220> FEATURE:

```
<223> OTHER INFORMATION: Description of Artificial Sequence: Synthetic
      DNA

<400> SEQUENCE: 18
ttgccatata tatatatata tataagtagg                                          30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19 tggttttgc catatatata tataagtagg                                           30
```